(12) United States Patent
Yoon

(10) Patent No.: US 10,893,885 B2
(45) Date of Patent: Jan. 19, 2021

(54) MULTI-NEEDLE ASSEMBLY FOR SUCTION INJECTOR

(71) Applicant: PANACE CO., LTD., Seongnam-si (KR)

(72) Inventor: Sung Tae Yoon, Seoul (KR)

(73) Assignee: PANACE CO., LTD., Seongnam-si (KR)

( * ) Notice: Subject to any disclaimer, the term of this patent is extended or adjusted under 35 U.S.C. 154(b) by 102 days.

(21) Appl. No.: 16/234,506

(22) Filed: Dec. 27, 2018

(65) Prior Publication Data

US 2020/0205852 A1 Jul. 2, 2020

(51) Int. Cl.
*A61B 17/34* (2006.01)

(52) U.S. Cl.
CPC .. *A61B 17/3421* (2013.01); *A61B 2017/3443* (2013.01)

(58) Field of Classification Search
CPC ............... A61B 17/34; A61B 17/3421; A61B 2017/3443; A61B 2017/00761; A61B 2017/00769; A61B 2017/00747; A61B 2017/00752; A61M 5/178; A61M 5/32; A61M 5/46; A61M 5/3295; A61M 37/0015; A61M 2037/0023
See application file for complete search history.

(56) References Cited

U.S. PATENT DOCUMENTS

| 8,920,379 | B2* | 12/2014 | Lee | A61M 37/0084 604/173 |
| 2014/0094742 | A1* | 4/2014 | Won | A61M 37/00 604/46 |
| 2015/0133862 | A1* | 5/2015 | Bang | A61M 37/0015 604/117 |
| 2015/0151098 | A1* | 6/2015 | Spendlove | A61M 37/0076 606/186 |

FOREIGN PATENT DOCUMENTS

| KR | 10-1106495 | 1/2012 |
| KR | 10-1398516 | 5/2014 |
| KR | 10-1508067 | 4/2015 |
| KR | 20-0484467 | 9/2017 |

* cited by examiner

*Primary Examiner* — Melanie R Tyson
(74) *Attorney, Agent, or Firm* — Rabin & Berdo, P.C.

(57) ABSTRACT

A multi-needle assembly for cosmetic procedure includes a main body having an inner space extending from one end to another, a reciprocating member provided in the main body, a needle member placed into the reciprocating member and having a plurality of needles that enter or exit through the one end of the main body, a guide suction into or from which the plurality of needles enter or exit, and length adjusting grooves for moving the reciprocating member in a forward and backward direction.

5 Claims, 5 Drawing Sheets

MULTI-NEEDLE ASSEMBLY FOR SUCTION INJECTOR

BACKGROUND

1. Field of the Invention

The present disclosure relates to a multi-needle assembly for cosmetic procedure, and more specifically, to a multi-needle assembly which is accurately adjustable in the depth to which it is injected into a skin, by a simple operation.

2. Description of the Related Art

The procedure of perforating a plurality of fine holes in skin and delivering medication therethrough (referred herein as 'multihole therapy') is used for a variety of purposes including treatment of skin troubles such as wrinkles, spots, blemishes, stretch marks, acne, freckles, pigmentation, and the like, maintenance of hair health and prevention of hair loss, treatment of obesity, or the like. The multihole therapy provides fast treatment effect by utilizing regenerating power of a damaged skin that regenerates new skin or by allowing medication or the like to be penetrated into the body through the fine holes. However, since the multihole therapy described above often relies on the intuition of a practitioner who manually repeats the needling operation, there are concerns that the medication may not be injected in an uniform amount, and that the skin of a patient loses appropriate skin firmness (i.e., tension) and stretched in the process of perforating massive fine holes in the skin, in which case needles are slid away and as a result, perforations are not formed in the accurate desired position in need of the treatment. In order to increase the effect of the treatment, it is necessary to adjust the exposure length of the needle since the injection depth of the drug needs to be changed according to the skin condition of a patient. However, the conventional multi-needle assembly having needles in the fixed exposure lengths is convenient to use since it requires the needles be replaced for use thereof, and the multi-needle assembly that is adjustable in the exposure length of the needle also has a drawback in that the needle can be bent in the process of adjusting due to complicated structure.

PRIOR ART DOCUMENT

Patent Literature

Korean Patent Registration No. 10-1106495
Korean Patent Registration No. 10-1508067
Korean Patent Registration No. 10-1398516
Korean Utility Model Registration No. 20-0484467

SUMMARY

The present disclosure has been made to overcome the problems of the related art discussed above, and accordingly, provides a multi-needle assembly for cosmetic procedure for a suction injector, which maintains a tension of the skin by suctioning a treatment area in the process of multihole therapy, and is accurately adjustable in a depth at which a needle is injected into a skin by a simple operation.

The object of the present disclosure described above can be achieved by a multi-needle assembly for cosmetic procedure, which may include a main body having an inner space extending from one to the other ends, a reciprocating member provided in the main body to be moved along an inner circumferential surface of the main body in a forward and backward direction, a needle member placed into the reciprocating member 4 and coupled therein, and having a plurality of needles that enter or exit through one end of the main body, a guide suction into or from which the plurality of needles enter or exit, in which the guide suction comprises an opening to be brought into contact with a skin and forms a suction force for sucking in foreign matter from inside while the opening is in close contact with the skin, and a length adjusting means for moving the reciprocating member in a forward and backward direction along a spiral groove and a slide groove formed in the inner circumferential surface of the main body to adjust a projecting length of the needles.

The reciprocating member may include a moving body having a receiving space formed therein and an opening formed in one side thereof, the moving body being coupled to the inner circumferential surface of the main body, a guide ring protruding along an outer circumferential surface of one end of the moving body to contact the inner circumferential surface of the main body, and a handle connected to the moving body and exposed to outside of the main body and having an opening formed therein, and may be moved within the main body by the length adjusting means.

The length adjusting means may include a first spiral groove inclined on the inner circumferential surface of the main body, a first slide groove connected to the first spiral groove and formed on the inner circumferential surface of the main body in a horizontal direction, a second spiral groove connected to an end of the first slide groove and inclined at the same angle as the first spiral groove, and a second slide groove connected to the second spiral groove and formed on the inner circumferential surface of the main body in a horizontal direction, in which the first and second spiral grooves and the first and second slide grooves may be continuously formed.

The guide suction may include an annular jaw protruding from an inner circumference of the opening, in which the annular jaw may include a planar portion formed thereon to be brought into close contact with the skin to allow the skin to be inserted into the opening in a vacuum state, resulting in an airtight state.

The guide suction may include a suction port formed on one side in a communication with the opening, and a blocking jaw formed in an aperture of the inner circumferential surface of the suction port to face the opening, in which ingress of impurity into the suction port can be blocked by the blocking jaw.

According to exemplary embodiments, the length of the reciprocating member can be adjusted by forward and reverse rotation and advancing and retreating movement in the main body, and there is an effect that the projecting depth of the needles can be accurately and precisely adjusted by setting the position of the needle member coupled thereto.

BRIEF DESCRIPTION OF THE DRAWINGS

The above and other objects, features and advantages of the present disclosure will become more apparent to those of ordinary skill in the art by describing in detail exemplary embodiments thereof with reference to the accompanying drawings, in which.

DETAILED DESCRIPTION

Hereinafter, preferred embodiments according to the present disclosure will be described in detail with reference to the accompanying drawings. The terms used herein are defined in consideration of the functions of the present disclosure, and they are should be construed to mean concepts that are in accordance with the technical idea of the present disclosure and interpreted in a way that is generally or commonly recognized in the art. Further, in explaining the present disclosure, any specific explanation on a well-known related configuration or function deemed to obscure the gist of the present disclosure will be omitted. Some of the attached drawings herein are exaggerated or simplified for convenience and clarity of explanation and understanding of the structure and operation of the technology, and each element may not exactly coincide with the actual size.

Figure 1:
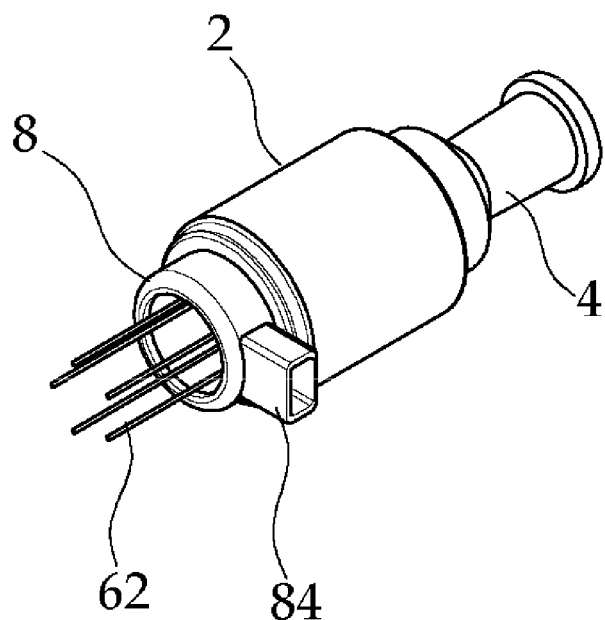
FIG. 1 is a perspective view showing a multi-needle assembly for cosmetic procedure according to an exemplary embodiment.
Figure 2:
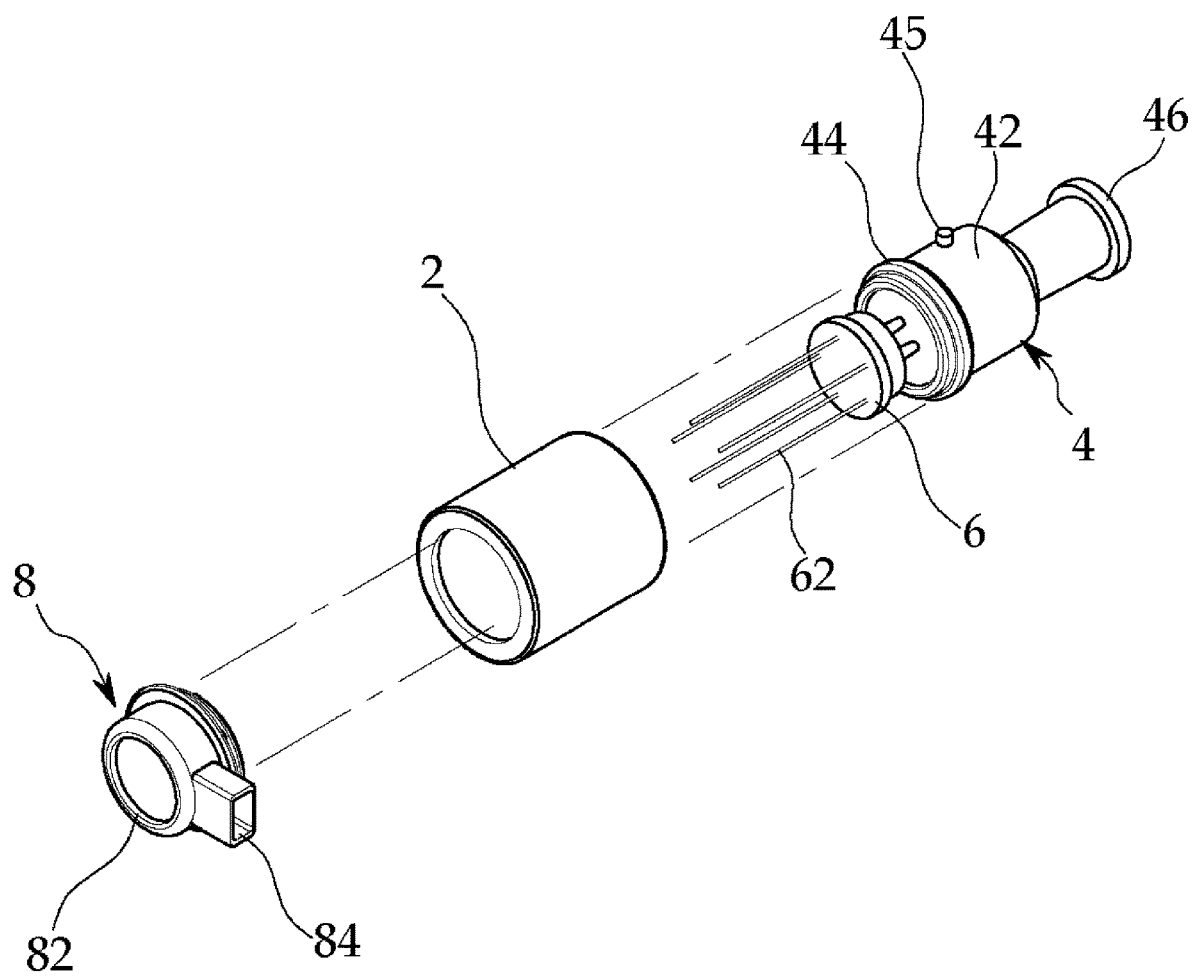
FIG. 2 is an exploded perspective view showing a multi-needle assembly for cosmetic procedure according to an exemplary embodiment.
Figure 3:
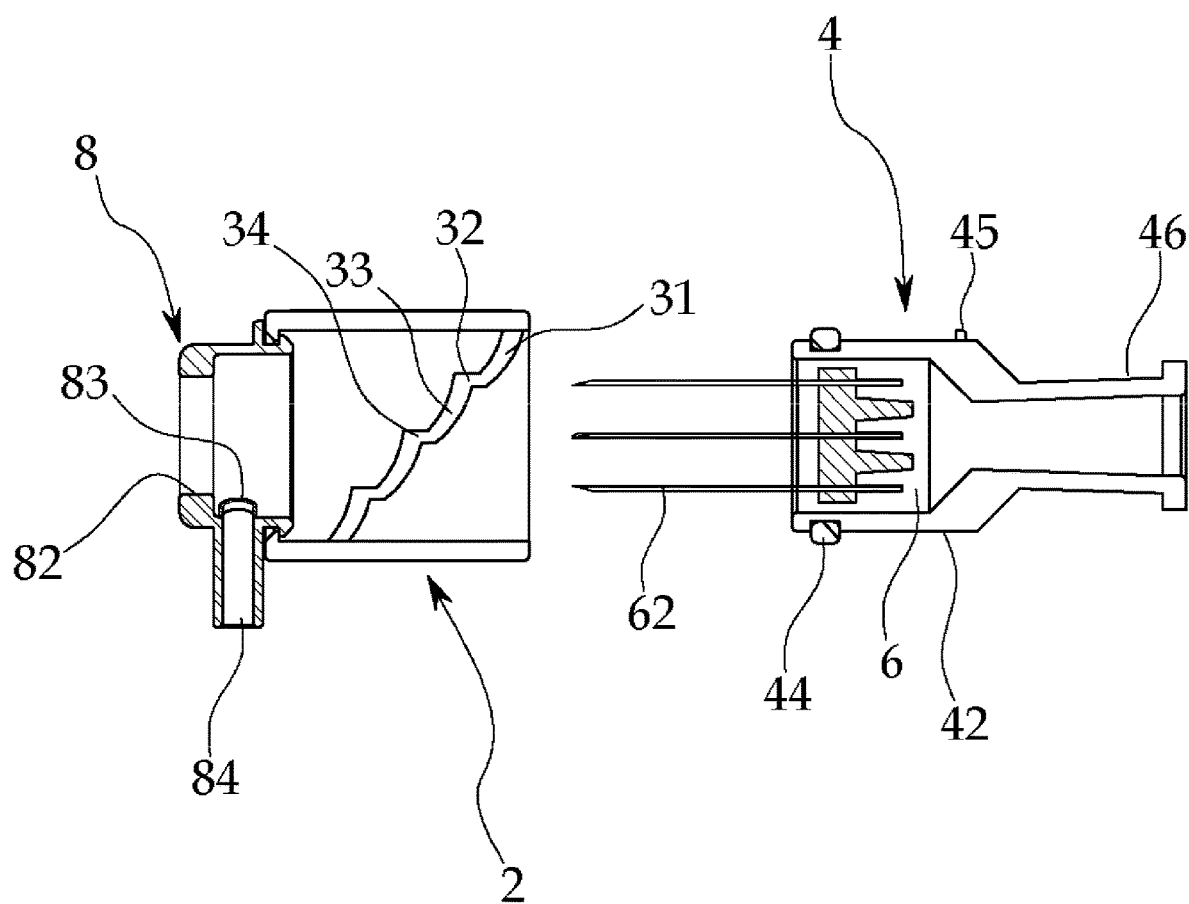
FIG. 3 is an exploded cross-sectional view showing a multi-needle assembly for cosmetic procedure according to an exemplary embodiment.
Figure 4:
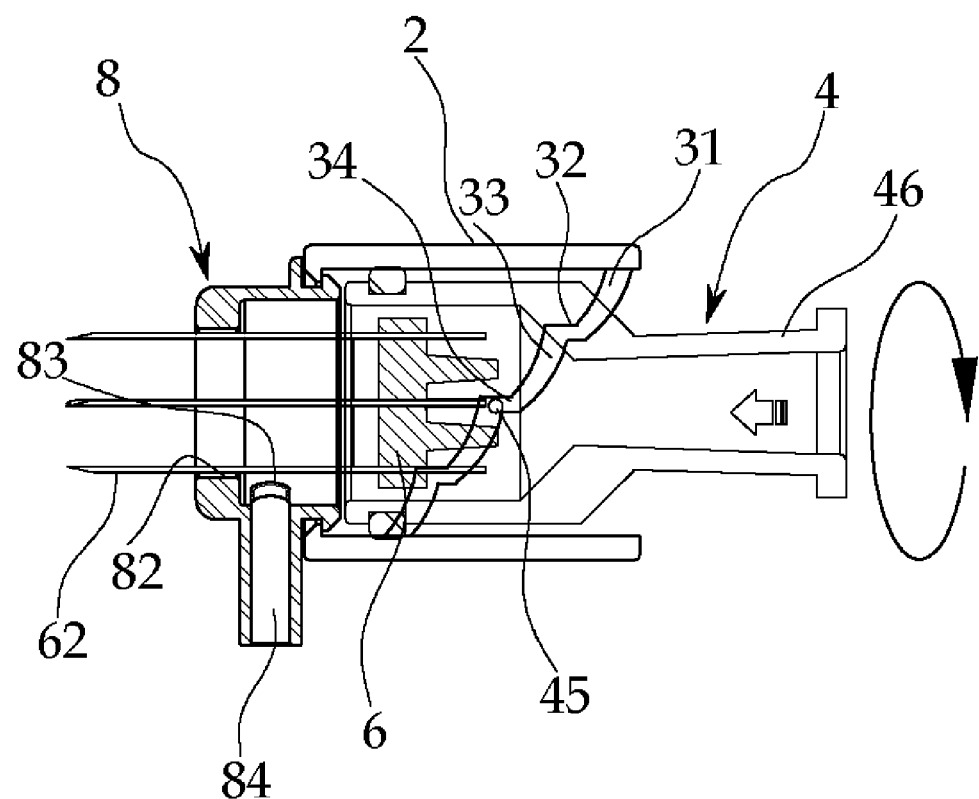
FIG. 4 is a cross-sectional view illustrating an advancing operation of a needle member of a multi-needle assembly for cosmetic procedure according to an exemplary embodiment.
Figure 5:
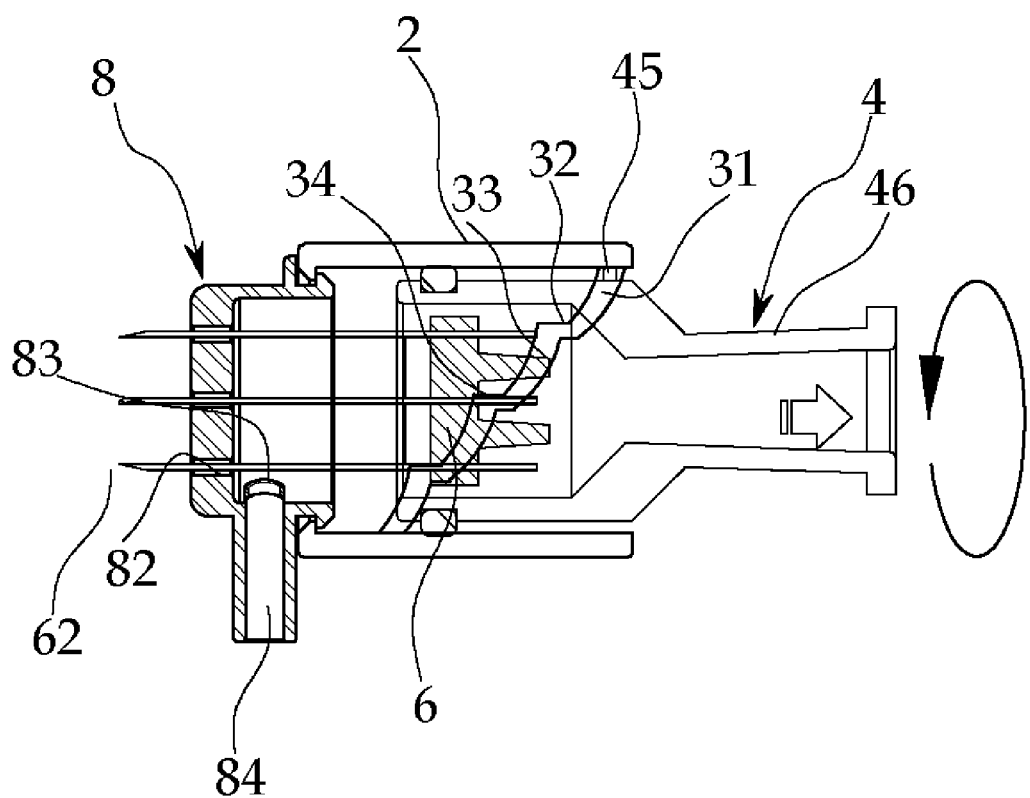
FIG. 5 is a cross-sectional view illustrating a retreating operation of a needle member of a multi-needle assembly for cosmetic procedure according to an exemplary embodiment.

In the accompanying drawings, FIG. 1 is a perspective view showing a multi-needle assembly for cosmetic procedure according to an exemplary embodiment, FIG. 2 is an exploded perspective view showing a multi-needle assembly for cosmetic procedure according to an exemplary embodiment, FIG. 3 is an exploded cross-sectional view showing a multi-needle assembly for cosmetic procedure according to an exemplary embodiment, FIG. 4 is a cross-sectional view illustrating an advancing operation of a needle member of a multi-needle assembly for cosmetic procedure according to an exemplary embodiment, and FIG. 5 is a cross-sectional view illustrating a retreating operation of a needle member of a multi-needle assembly for cosmetic procedure according to an exemplary embodiment.

As shown in FIGS. 1 to 5, the multi-needle assembly for cosmetic procedure according to an exemplary embodiment includes a main body 2 having an inner space extending from one to the other ends, a reciprocating member 4 provided in the main body 2 to be moved along an inner circumferential surface of the main body 2 in a forward and backward direction, a needle member 6 placed into the reciprocating member 4 and coupled therein, and having a plurality of needles 62 that enter or exit through one end of the main body 2, and a guide suction 8 into or from which the plurality of needles 62 enter or exit, in which the guide suction 8 includes an opening to be brought into contact with the skin, and forms a suction force for sucking in foreign matter from inside while the opening is in close contact with the skin.

In addition, the multi-needle assembly for cosmetic procedure according to the present disclosure includes a length adjusting means including a spiral groove formed in the inner circumferential surface of the main body 2, a slide groove, and a protrusion 45 formed on an outer circumferential surface of the reciprocating member 4 to be inserted into the spiral groove and the slide groove, in which the reciprocating member 4 is moved along the spiral groove and the slide groove in a forward and backward direction to adjust the projecting length of the needles 62.

The main body 2 has a shape of a cylinder with both ends open, and the guide suction 8 is coupled by tight fit to one opening of the main body 2.

For convenience of explanation, the direction in which the needles 62 are protruded will be referred to as a front direction, and the side opposite thereto will be referred to as a rear direction.

The reciprocating member 4 coupled with the needle member 6 is coupled to the rear opening of the main body 2, and the guide suction 8 is coupled to the front opening of the main body 2.

The reciprocating member 4 includes a moving body 42 having a receiving space formed therein and an opening formed in one side thereof, and being coupled to the inner circumferential surface of the main body 2, a guide ring 44 protruding along an outer circumferential surface of one end of the moving body 42 and contacting the inner circumferential surface of the main body 2, and a handle 46 connected to the moving body 42 and exposed to outside of the main body 2 and having an opening formed therein, and is moved within the main body 2 by the length adjusting means.

The moving body 4 has a cylindrical shape having an outer diameter corresponding to an inner diameter of the main body 2. A handle 46 is continuously formed on the rear side of the moving body 4, and has a diameter significantly reduced from that of the moving body 42.

As shown in FIG. 3, the length adjusting means includes a first spiral groove 31 inclined on the inner circumferential surface of the main body 2, a first slide groove 32 connected to the first spiral groove 31 and formed on the inner circumferential surface of the main body 2 in a horizontal direction, a second spiral groove 33 connected to an end of the first slide groove 32 and inclined at the same angle as the first spiral groove 31, and a second slide groove 34 connected to the second spiral groove 33 and formed on the inner circumferential surface of the main body 2 in a horizontal direction.

The first and second spiral grooves 31 and 33 and the first and second slide grooves 32 and 34 described above may be formed as a set, and these sets may be formed continuously.

The protrusion 45 is formed on the outer circumferential surface of the moving body 42 of the reciprocating member 4 to be inserted into the first and second spiral grooves 31 and 33 or the first and second slide grooves 32 and 34. The first and second spiral grooves 31 and 33 cause the reciprocating member 4 to be rotated and moved forward or backward while being rotated. The first and second slide grooves 32 and 34 cause the reciprocating member 4 to be linearly moved or backward. The protrusion 45 of the reciprocating member 4 may be moved forward or backward while being rotated along the first spiral groove 31 and then moved forward or backward along the first slide groove 32 so that the projecting length of the needle 62 can be adjusted.

In addition, the protrusion 45 of the reciprocating member 4 is moved along the second spiral groove 33 and the second slide groove 34, and thus enables continuous adjustment of the protruding length of the needles 62 to a longer length.

Referring to FIG. 3, the guide suction 8 includes an annular jaw 82 protruding from an inner circumference of the opening.

The annular jaw 82 has a planar portion formed on a front surface to be brought into close contact with the skin. Therefore, when the guide suction 8 is brought into close contact with the skin and the vacuum pressure is formed, the skin is inserted into the opening in the vacuum state, and the planar portion of the annular jaw 82 can achieve a completely close contact with the skin and thus maintain the airtight state.

The guide suction 8 includes a suction port 84 formed on one side in a communication with the opening, and a blocking jaw 83 formed in an aperture of the inner circumferential surface of the suction hole 84 to face the opening.

Therefore, ingress of impurities into the suction port 84 can be blocked by the blocking jaw 83.

Hereinafter, the operation of the embodiment of the present disclosure will be described.

The reciprocating member 4 is coupled to the main body 2 through the rear opening thereof. When the needle member 6 is placed into the reciprocating member 4 and coupled therein, a plurality of needles 62 may be faced forward and protruded through the opening of the guide suction 8. The guide suction 8 is coupled to the front opening of the main body 2. When a user grabs the rear handle 46 of the reciprocating member 4 including the needle member 6 and rotates it in one direction, the protrusion 45 is rotated along the first spiral groove 31, which may result in a primary advancing operation of the reciprocating member 4. Then, when the user pushes the handle 46 after the protrusion 45 reaches an end of the first spiral groove 31, the protrusion 45 is moved forward along the first slide groove 32, resulting in a secondary advancing operation of the reciprocating member 4.

The advancing operation of the reciprocating member 4 can be additionally realized as necessary, by moving the reciprocating member 4 along the second spiral groove 33 and the second slide groove 34 in the manner described above. The advancing operation described above can be performed stepwise by continuously performing the rotational and the linear movement.

On the contrary, when the handle 46 of the reciprocating member 4 is pulled, the backward movement is performed in the reverse order of the process described above, and as a result, a stepwise backward operation is realized. Therefore, it is possible to easily adjust the protruding length of the needles 62 by finely adjusting the position of the reciprocating member 4, and thus set the depth of the needles 62 inserted into the skin to an appropriate depth.

While the present disclosure has been particularly shown and described with reference to exemplary embodiments thereof, it is to be understood that the disclosure is not limited to the disclosed exemplary embodiments, but is rather intended to cover various modifications and equivalent arrangements without departing from the spirit and scope of the appended claims, and can be modified by substitutions of the elements and other equivalent embodiments, and accordingly, it should be understood that numerous other modifications and applications fall within the spirit and scope of the principles of this disclosure.

[Description of the Reference Numerals]

| | | |
|---|---|---|
| 2: Main body | 4: Reciprocating member | 6: Needle member |
| 8: Guide suction | 31: First spiral groove | 32: First slide groove |
| 33: Second spiral groove | 34: Second slide groove | 42: Moving body |
| 44: Guide ring | 46: Handle | 45: Protrusion |
| 82: Annular jaw | | |

What is claimed is:

1. A multi-needle assembly for cosmetic procedure, comprising:
    a main body having an inner space extending from one end to another end of the main body;
    a reciprocating member provided in the main body to be moved along an inner circumferential surface of the main body in a forward and backward direction;
    a needle member placed into the reciprocating member and coupled to the reciprocating member, and having a plurality of needles that enter or exit through the one end of the main body;
    a guide suction into or from which the plurality of needles enter or exit, wherein the guide suction comprises an opening to be brought into contact with a skin and forms a suction force for sucking in foreign matter from inside the skin while the opening is in close contact with the skin;
    length adjusting grooves for moving the reciprocating member in flail the forward and backward direction, the length adjusting grooves including at least one spiral groove and flail at least one slide groove formed in the inner circumferential surface of the main body to adjust a projecting length of the needles; and
    a protrusion formed on an outer circumferential surface of the reciprocating member for moving the reciprocating member in the forward and backward direction along the at least one spiral groove and the at least one slide groove to adjust a projecting length of the needles.

2. The multi-needle assembly for cosmetic procedure according to claim 1, wherein the reciprocating member comprises:
    a moving body having a receiving space formed therein and an opening formed in one side thereof, the moving body being coupled to the inner circumferential surface of the main body;
    a guide ring protruding along an outer circumferential surface of one end of the moving body to contact the inner circumferential surface of the main body; and
    a handle connected to the moving body and exposed to outside of the main body and having an opening formed therein, and being configured to be moved within the main body by the length adjusting grooves.

3. The multi-needle assembly for cosmetic procedure according to claim 2, wherein the at least one spiral groove and the at least one slide groove comprise a first spiral groove inclined on the inner circumferential surface of the main body, a first slide groove connected to the first spiral groove and formed on the inner circumferential surface of the main body in a horizontal direction, a second spiral groove connected to an end of the first slide groove and inclined at the same angle as the first spiral groove, and a second slide groove connected to the second spiral groove and formed on the inner circumferential surface of the main body in flail the horizontal direction,
    wherein the first and second spiral grooves and the first and second slide grooves are continuously formed.

4. The multi-needle assembly for cosmetic procedure according to claim 1, wherein the guide suction comprises an annular jaw protruding from an inner circumference of the opening, and
    wherein the annular jaw comprises a planar portion formed thereon to be brought into close contact with the skin to allow the skin to be inserted into the opening in a vacuum state, resulting in an airtight state.

5. The multi-needle assembly for cosmetic procedure according to claim 1, wherein the guide suction comprises:
a suction port formed on one side of the guide suction, in flail communication with the opening; and
a blocking jaw formed in an aperture of an inner circumferential surface of the suction port facing the opening,
wherein ingress of impurity into the suction port is blocked by the blocking jaw.

\* \* \* \* \*